US008685079B2

(12) United States Patent
Leynov et al.

(10) Patent No.: US 8,685,079 B2
(45) Date of Patent: *Apr. 1, 2014

(54) EXPANDABLE FRAMEWORK WITH OVERLAPPING CONNECTORS

(71) Applicant: Boston Scientific Scimed, Inc., Maple Grove, MN (US)

(72) Inventors: Alexander Leynov, Walnut Creek, CA (US); Delilah Yin Hui, American Canyon, CA (US); David C. Barry, Livermore, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/646,919

(22) Filed: Oct. 8, 2012

(65) Prior Publication Data

US 2013/0060322 A1   Mar. 7, 2013

Related U.S. Application Data

(63) Continuation of application No. 12/826,217, filed on Jun. 29, 2010, now Pat. No. 8,287,588, which is a continuation of application No. 10/895,815, filed on Jul. 21, 2004, now Pat. No. 7,744,641.

(51) Int. Cl.
*A61F 2/86* (2013.01)

(52) U.S. Cl.
USPC ........................................... 623/1.15

(58) Field of Classification Search
USPC .................... 623/1.15, 1.16, 1.18, 1.2, 1.3
See application file for complete search history.

(56) References Cited

U.S. PATENT DOCUMENTS

| 5,383,892 | A | | 1/1995 | Cardon et al. | |
|---|---|---|---|---|---|
| 5,449,373 | A | * | 9/1995 | Pinchasik et al. | 606/198 |
| 5,755,776 | A | | 5/1998 | Al-Saadon | |
| 5,769,887 | A | | 6/1998 | Brown et al. | |
| 5,817,126 | A | | 10/1998 | Imran | |
| 5,868,783 | A | * | 2/1999 | Tower | 606/198 |
| 5,947,962 | A | | 9/1999 | Guglielmi et al. | |
| 5,980,552 | A | * | 11/1999 | Pinchasik et al. | 623/1.16 |
| 6,019,789 | A | * | 2/2000 | Dinh et al. | 623/1.15 |
| 6,059,811 | A | | 5/2000 | Pinchasik et al. | |
| 6,171,334 | B1 | * | 1/2001 | Cox | 623/1.15 |
| 6,190,403 | B1 | | 2/2001 | Fischell et al. | |
| 6,193,744 | B1 | * | 2/2001 | Ehr et al. | 623/1.16 |
| 6,231,598 | B1 | * | 5/2001 | Berry et al. | 623/1.15 |
| 6,238,409 | B1 | * | 5/2001 | Hojeibane | 606/194 |
| 6,270,524 | B1 | * | 8/2001 | Kim | 623/1.15 |

(Continued)

FOREIGN PATENT DOCUMENTS

| WO | 95/26695 | 10/1995 |
|---|---|---|
| WO | 97/32543 | 9/1997 |
| WO | 01/85046 | 11/2001 |

*Primary Examiner* — Ryan Severson
(74) *Attorney, Agent, or Firm* — Vidas, Arrett & Steinkraus

(57) ABSTRACT

A stent may comprise a plurality of serpentine bands and connectors. A first connector may overlap a second connector when the stent is unexpanded. The first connector may also overlap the second connector in an unexpanded state when the stent is subject to compressive forces in the local area of the connectors, such as when the connectors are located on the inside of a curve. The second connector may be shaped according to a rotation of the first connector about the centroid of the cell between the first connector and the second connector.

15 Claims, 4 Drawing Sheets

(56) References Cited

U.S. PATENT DOCUMENTS

| | | |
|---|---|---|
| 6,340,366 B2* | 1/2002 | Wijay ............................ 623/1.13 |
| 6,375,677 B1 | 4/2002 | Penn et al. |
| 6,383,216 B1 | 5/2002 | Kavteladze et al. |
| 6,416,539 B1* | 7/2002 | Hassdenteufel ............. 623/1.15 |
| 6,428,569 B1 | 8/2002 | Brown |
| 6,464,720 B2* | 10/2002 | Boatman et al. ............. 623/1.15 |
| 6,485,510 B1* | 11/2002 | Camrud et al. ............... 623/1.16 |
| 6,508,834 B1* | 1/2003 | Pinchasik et al. ............ 623/1.16 |
| 6,547,818 B1 | 4/2003 | Rourke et al. |
| 6,565,597 B1 | 5/2003 | Fearnot et al. |
| 6,579,310 B1 | 6/2003 | Cox et al. |
| 6,673,106 B2 | 1/2004 | Mitelberg et al. |
| 6,974,471 B2* | 12/2005 | Van Schie et al. ............ 623/1.12 |
| 7,060,089 B2 | 6/2006 | Ley et al. |
| 7,179,286 B2* | 2/2007 | Lenz ............................. 623/1.15 |
| 7,744,641 B2 | 6/2010 | Leynov et al. |
| 7,942,920 B2* | 5/2011 | Majercak ..................... 623/1.15 |
| 8,287,588 B2* | 10/2012 | Leynov et al. ................ 623/1.15 |
| 2002/0010507 A1 | 1/2002 | Ehr et al. |
| 2002/0013617 A1* | 1/2002 | Matsutani et al. ............ 623/1.15 |
| 2002/0120327 A1* | 8/2002 | Cox et al. ..................... 623/1.16 |
| 2003/0055489 A1* | 3/2003 | Kveen et al. .................. 623/1.15 |
| 2003/0078649 A1* | 4/2003 | Camrud et al. ............... 623/1.16 |
| 2003/0088305 A1 | 5/2003 | Van Schie et al. |
| 2003/0139799 A1 | 7/2003 | Ley et al. |
| 2003/0176914 A1 | 9/2003 | Rabkin et al. |
| 2003/0212449 A1* | 11/2003 | Cox .............................. 623/1.15 |
| 2004/0093073 A1* | 5/2004 | Lowe et al. .................. 623/1.15 |
| 2004/0167609 A1* | 8/2004 | Majercak ..................... 623/1.15 |
| 2004/0204752 A1* | 10/2004 | Ehr et al. ...................... 623/1.15 |
| 2004/0215326 A1* | 10/2004 | Goodson et al. ............. 623/1.16 |
| 2004/0230291 A1* | 11/2004 | Richter ......................... 623/1.15 |
| 2004/0236406 A1* | 11/2004 | Gregorich .................... 623/1.16 |
| 2004/0260387 A1 | 12/2004 | Regala et al. |
| 2005/0187606 A1* | 8/2005 | Gregorich .................... 623/1.15 |
| 2005/0222670 A1* | 10/2005 | Schaeffer ..................... 623/1.15 |
| 2006/0020322 A1* | 1/2006 | Leynov et al. ................ 623/1.15 |
| 2006/0030925 A1* | 2/2006 | Pryor ............................ 623/1.12 |
| 2006/0069424 A1* | 3/2006 | Acosta et al. ................. 623/1.12 |
| 2007/0213810 A1* | 9/2007 | Newhauser et al. .......... 623/1.16 |
| 2010/0268326 A1* | 10/2010 | Leynov et al. ................ 623/1.16 |
| 2013/0060322 A1* | 3/2013 | Leynov et al. ................ 623/1.16 |

* cited by examiner

EXPANDABLE FRAMEWORK WITH OVERLAPPING CONNECTORS

CROSS-REFERENCE TO RELATED APPLICATIONS

This application is a Continuation application that claims the benefit of U.S. patent application Ser. No. 12/826,217, now U.S. Pat. No. 8,287,588, which is a Continuation application that claims the benefit of U.S. patent application Ser. No. 10/895,815, now U.S. Pat. No. 7,744,641, the entire content of which is hereby incorporated herein by reference.

BACKGROUND OF THE INVENTION

The use of stents in bodily lumen is well known. A stent is typically delivered in an unexpanded state to a desired location in a bodily lumen via a stent delivery device such as a catheter. Once the stent is at the desired bodily location, it is either expanded with a balloon or other suitable device or allowed to expand by, for example, withdrawing a restraining sheath.

Some stents may be used to place Guglielmi electrolytically detachable coils, for example as described in U.S. Pat. No. 5,947,962, incorporated herein by reference.

Stents are desirably flexible in order to be delivered through a tortuous anatomy. As the amount of curvature along the length of a stent is increased, some stents may reach a point where adjacent struts contact one another. If the amount of curvature is further increased, the stent may undesirably kink.

There remains a need for a stent that may be maneuvered through areas of high curvature. There remains a need for a stent that may be deployed at an area of high curvature.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In one embodiment, a stent may comprise a plurality of serpentine bands. Adjacent serpentine bands may be connected by connectors. A first connector and a second connector may overlap in a radial direction of the stent when the stent is expanded and deployed on a curve. The first connector and the second connector may overlap in a radial direction of the stent when the stent is unexpanded. The amount of overlap may increase as the degree of curvature along the longitudinal axis of the stent increases when the stent is expanded. The amount of overlap between the first connector and the second connector may be measured in a stent circumferential direction.

The edges of the first connector and the second connector may be rounded to encourage overlap and reduce binding. The width of a serpentine band strut may be greater than the width of a connector.

In some embodiments, a serpentine band strut may have a width:thickness ratio of 1:1. The first connector may have a width:thickness ratio of 0.75:1.

In some embodiments, the shape and orientation of the first connector and the second connector may be related through a symmetry operation. The second connector may be a rotation of the first connector. The rotation may be a half-turn about the centroid of a cell between the first connector and the second connector.

In some embodiments, the stent may further comprise a third connector and a fourth connector. The third connector may be a reflection of the first connector, and the fourth connector may be a reflection of the second connector.

In some embodiments, the serpentine bands may each comprise alternating peaks and valleys. Each peak and valley located on the interior of the stent may be connected to a connector. In some embodiments, every other peak of a serpentine band may be connected to two connectors.

In some embodiments, a stent may comprise an expandable framework comprising a plurality of serpentine bands and a plurality of connectors including a first set of connectors and a second set of connectors. A connector of the first set may overlap a connector of the second set in a radial direction of the stent when the stent is expanded and deployed on a curve.

In some embodiments, the first set of connectors may include first, second and third connectors. The second set of connectors may include fourth, fifth and sixth connectors. The third connector may overlap the fourth connector in a radial direction of the stent when the stent is expanded and deployed on a curve. The first connector and the fourth connector may be shaped and oriented similarly. The second connector and the fifth connector may be shaped and oriented similarly. The third connector and the sixth connector may be shaped and oriented similarly.

In some embodiments, the fourth connector may be shaped according to a rotation of the third connector about the centroid of a cell located between the third connector and fourth connector. The third connector may be shaped according to a rotation of the first connector about the centroid of an area consisting of the two cells between the first connector and the third connector.

In some embodiments, each connector may include at least one peak.

In some embodiments, the amount of overlap between adjacent struts may increase as the amount of curvature of the stent along its longitudinal axis increases. Overlap between adjacent struts may be measured in a stent circumferential direction.

In some embodiments, a stent may comprise an expandable framework having a plurality of cells and a plurality of serpentine bands connected by connectors. A first connector may include at least one peak, and a second connector may be shaped according to a rotation of the first connector about the centroid of a cell. The connectors may further include at least one inflection point. The first connector and the second connector may overlap in a radial direction of the stent when the stent is unexpanded. The first connector and the second connector may overlap when the stent is expanded and subject to bending along the longitudinal axis.

In some embodiments, the stent may further comprise a second cell of different shape than the first cell, a third connector and a fourth connector. The third connector may be a rotation of the second connector about a centroid of the second cell. The fourth connector may be a rotation of the first connector about the centroid of the second cell.

In some embodiments, when curvature is applied to the stent along its length, the second connector and the third connector may move away from one another, and the first connector and the second connector may move toward one another. Each connector may have an axial component and a circumferential component. When bending of the stent along a stent longitudinal axis is increased, the axial component of the first connector may be reduced and the circumferential component may increase.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there are illustrated and described various embodiments of the invention.

BRIEF DESCRIPTION OF THE DRAWINGS

A detailed description of the invention is hereafter described with specific reference being made to the drawings.

DETAILED DESCRIPTION OF THE INVENTION

Figure 1:
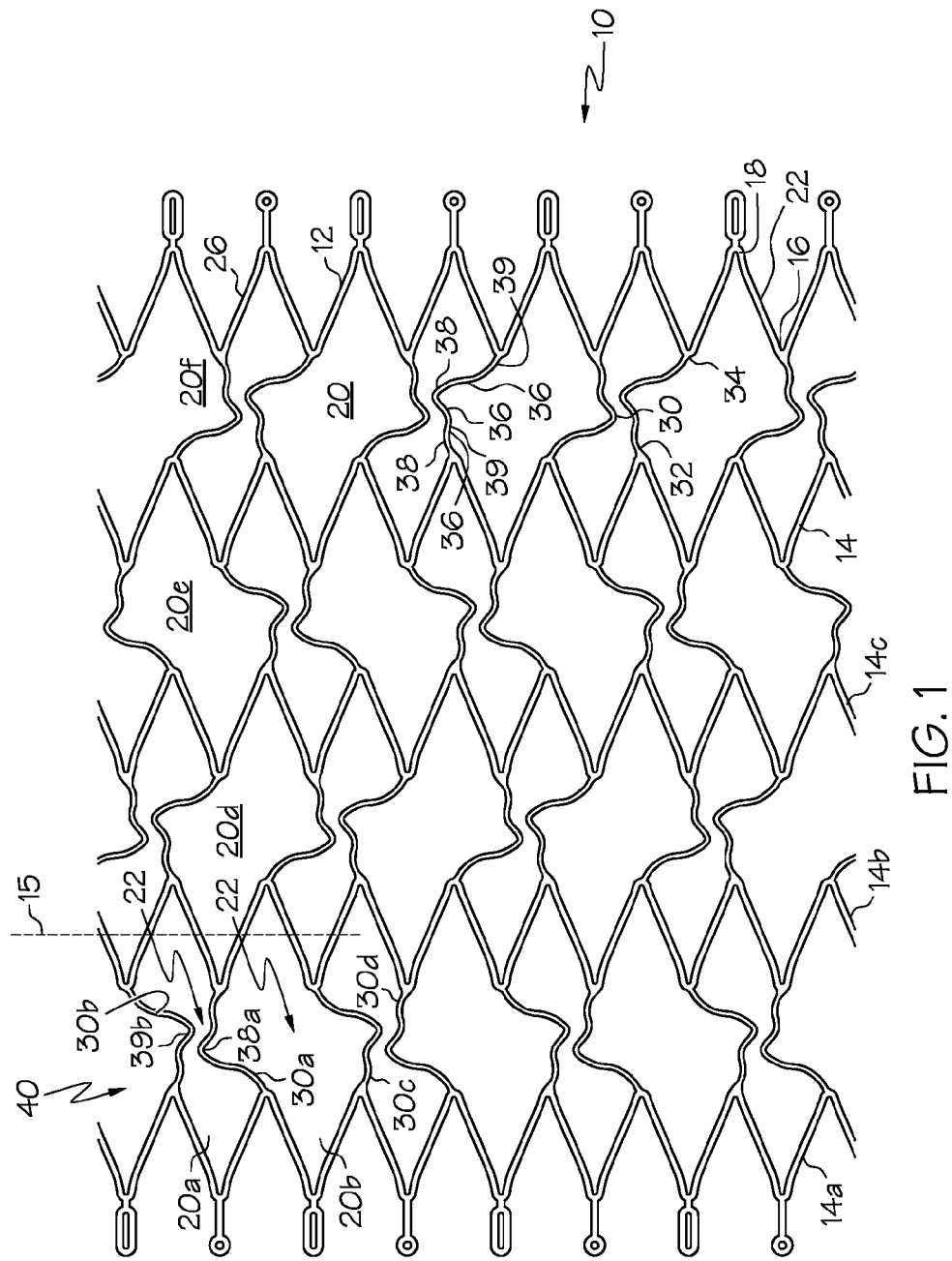
FIG. 1 is a flat pattern of an embodiment of a stent.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

The term "stent" as used herein is intended to encompass traditional stents suitable for supporting a vessel wall and other expandable framework or expanded devices for use within a bodily lumen. For example, an expandable framework according to the invention may be used to position and hold Guglielmi detachable coils. In some embodiments, an expandable framework for use with Guglielmi detachable coils may not be intended for supporting a vessel wall. Any shape configuration described herein may be used in some embodiments to form a stent for supporting a vessel wall, and may be used in some embodiments to form an expandable framework for placing Guglielmi detachable coils.

FIG. 1 shows a flat pattern for an embodiment of an inventive stent 10. The stent 10 may comprise an expandable framework 12 having a plurality of cells 20. The framework 12 may include a plurality of serpentine bands 14 and a plurality of connectors 30. Each serpentine band 14 may have alternating peaks 16 and valleys 18 connected by struts 26. Each connector 30 may connect at the first end 32 to one serpentine band 14 and may connect at the second end 34 to an adjacent serpentine band. Connectors 34 may connect to a serpentine band 14 at any portion of the band 14, and desirably at the peaks 16 and valleys 18.

Connectors 30 may be curved along their length and desirably include at least one peak 38. In some embodiments, connectors 30 may include at least one inflection point 36 or multiple inflection points 36. Connectors may further include any number of peaks 38 and/or valleys 39.

A first connector 30a and a second connector 30b may comprise a pair 40 of connectors. Connectors 30 of a pair 40 may move toward one another or away from one another as the stent 10 experiences various bending deformations along its length. Connectors 30 of a pair 40 may be arranged to overlap one another in one or more locations under certain conditions, such as when the stent is in an unexpanded state or when the stent is under curvature in an expanded state. Overlap may be in a radial direction of the stent 10.

The term "overlap" as used herein is intended to describe an overlapping relationship between two stent elements. Thus, when a first connector and second connector overlap in a stent radial direction, a radial line extending outwardly from the stent longitudinal axis in a stent radial direction may intersect the first connector and the second connector. Portions of the connectors which overlap in a radial direction may be circumferentially and longitudinally aligned on the stent, but are at different distances from the stent longitudinal axis. For the purposes of this disclosure, stent elements that are located on opposite sides of the stent across the stent longitudinal axis do not overlap one another.

Desirably, a serpentine band 14 forms a closed path about the longitudinal axis of the stent 10.

Figure 2:
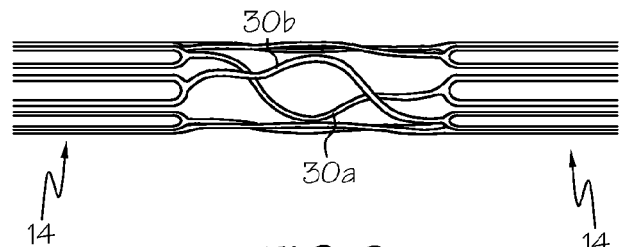
FIG. 2 shows a portion of a stent in an unexpanded state.

FIG. 2 shows an embodiment of a stent 10 in an unexpanded state. A first connector 30a may be arranged to overlap a second connector 30b while the stent 10 is unexpanded.

Figure 3:
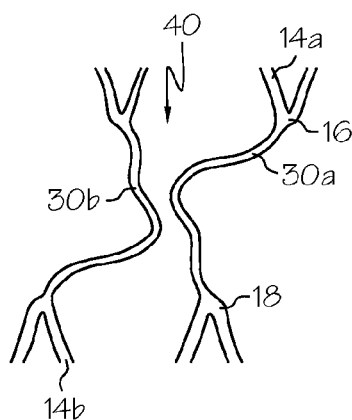
FIG. 3 shows two adjacent connectors when the stent is not subject to bending along the longitudinal axis.
Figure 4:
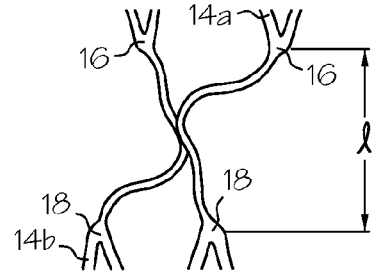
FIG. 4 shows two adjacent connectors that have begun to overlap when the stent is subject to bending along the longitudinal axis.
Figure 5:
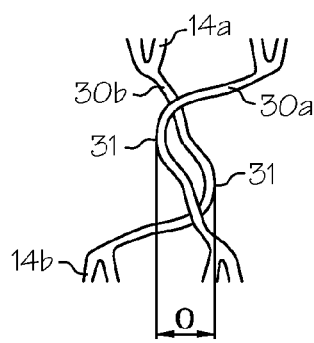
FIG. 5 shows two adjacent connectors that have a greater amount of overlap when the stent is subject to more bending than FIG. 4.

FIGS. 3-5 show a portion of an embodiment of a stent 10 in an expanded state as the stent 10 is subject to varying amounts of curvature along its length. FIG. 3 shows the placement of a first connector 30a and a second connector 30b when the stent is expanded and not subject to curvature. The connectors 30a, 30b may be arranged to connect a first serpentine band 14a to a second serpentine band 14b. As a stent 10 is subject to bending deformations, localized areas of the stent 10 on the outside of the curve may be placed in tension, while localized areas of the stent 10 on the inside of the curve may be placed in compression. Compressive forces may cause a serpentine band 14 to move closer to an adjacent serpentine band 14. Compressive forces may also cause the peaks 16 or valleys 18 of a given serpentine band 14 to move toward one another. Moving adjacent serpentine bands 14 toward one another may cause the first connector 30a and the second connector 30b to overlap. Moving the peaks 16 or valleys 18 of a serpentine band together may also cause the first connector 30a and the second connector 30b to overlap.

FIG. 4 shows a portion of the stent 10 when the stent 10 is subject to a bending deformation along its length. All of the elements shown in FIG. 4 may be subject to compressive forces. The first serpentine band 14a and the second serpentine band 14b may have moved toward one another as compared with FIG. 3. The peaks 16 of the first serpentine band 14a may have moved toward one another, and the valleys 18 of the second serpentine band 14b may also have moved toward one another. Each connector 30 may have an axial length component l measured in a direction parallel to the longitudinal axis of the stent. The axial length component l is a measurement of the span of the connector in an axial direction of the stent, which may be measured as the axial distance between a circumference of the stent which includes the most proximal point of the connector 30 and a circumference of the stent which includes the most distal point of the connector 30. The axial length component l of the first connector 30a may be reduced from that of FIG. 3. The first connector 30a and the second connector 30b have moved toward one another as the serpentine bands 14 have changed shape. The first connector 30a has begun to overlap the second connector 30b.

FIG. 5 shows a portion of the stent 10 when the stent 10 is subject to greater bending deformations than shown in FIG. 4. The first serpentine band 14a and the second serpentine band 14b have moved further toward one another. Thus, the axial length component l of the first connector 30a has been further reduced. The peaks 16 of the first serpentine band 14a have again moved toward one another, as have the valleys 18 of the second serpentine band 14b. The amount of overlap O between the first connector 30a and the second connector 30b has increased. Overlap O may be measured between the outward edges 31 of the overlapping connectors 30a, 30b in a stent circumferential direction, which may be orthogonal to the axial length component l of a connector 30. The amount of overlap O may be the circumferential component of a line extending between the outward edges of the overlapping connectors 30a, 30b, measured orthogonally to the stent longitudinal axis. The amount of overlap O between a pair 40 of connectors may increase as the stent 10 is subject to greater amounts of bending.

In some embodiments, connectors 30 may overlap when the stent 10 is subject to compressive forces. When a stent 10 experiences curvature along its length, generally the inside of the curve is subject to compressive forces and the outside of the curve is subject to tension. Thus, overlapping connectors 30 may be located at portions of a stent located toward the inside of a curve.

Figure 6:
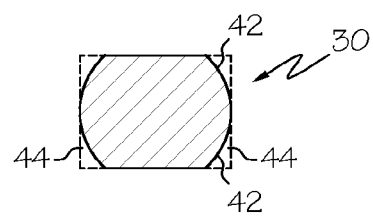
FIG. 6 shows a cross-section of a connector.

FIG. 6 shows a cross-section of an embodiment of a connector 30. In some embodiments, connectors 30 may have rounded edge portions 42, which may help adjacent connectors 30 to overlap. As a stent 10 is subject to bending, adjacent connectors 30 may move toward one another and eventually contact one another. As bending increases, rounded edge portion 42 help to allow the connectors 30 to slide over one another and overlap without binding. Connectors 30 may have any suitable cross-sectional shape. By way of non-limiting example, connectors 30 may be circular, oval, triangular or rectangular. Trapezoidal and rectangular struts whose cross-section includes angular regions may be modified by rounding the corners.

Connector 30 edges may be rounded using any suitable processing method, including but not limited to sandblasting, brushing, chemical etching, electropolishing and the like. Desirably, waste portions 44 may be removed during the process.

In some embodiments, connectors 30 may be less wide than other framework 12 elements. For example, the width:thickness ratio of portions of a serpentine band 14 may be 1:1, while the width:thickness ratio of a connector 30 may be 0.75:1. Thickness may be measured in a stent radial direction, while width may be measured in a direction across the width of the framework element in a direction orthogonal to the thickness.

In some embodiments, multiple pairs 40 of connectors 30 may overlap when the stent 10 is deployed on a curve.

In some embodiments, one or more serpentine bands 14 may form a continuous closed loop about a longitudinal axis of the stent 10.

In some embodiments, the stent 10 may comprise a framework 12 that is not woven, braided, coiled or folded over itself. For example, the stent 10 may be arranged such that no portion of a first serpentine band 14 overlaps another portion of the first serpentine band 14 in a radial direction of the stent 10.

Referring again to FIG. 1, a first connector 30a and a second connector 30b may form a pair 40 of adjacent connectors. The first connector 30a may include a main peak 38a, and the second connector 30b may include a main valley 39b. Desirably, the main peak 38a may be offset from the main valley 39b along the length of the stent 10. As the stent 10 is subject to bending and the axial length component l (see FIG. 4) of the connectors 30a, 30b is reduced, the connectors 30a, 30b may begin to deflect and buckle toward one another. The main peak 38a may be the point of greatest deflection for the first connector 30a, and the main valley 39b may be the point of greatest deflection for the second connector 30b. Because the stent 10 is substantially cylindrical, the main peak 38a and the main valley 39b may deflect slightly in an outward radial direction of the stent 10. Offsetting the main peak 38a from the main valley 39b along the length of the stent 10 will help the pair 40 of connectors 30 overlap without binding when the stent 10 is subject to bending.

In some embodiments, the stent 10 may have a plurality of cells 20, including a first cell 20a having a first shape and a second cell 20b having a second shape. First cells 20a and second cells 20b may alternate as the stent 10 is traversed in a circumferential direction.

Each cell 20 may have a center or centroid 22. A first connector 30a may have any suitable shape and desirably includes at least one peak 38. A first connector 30a may connect a first serpentine band 14a to a second serpentine band 14b. The first connector 30a may bound a portion of the first cell 20a, and a second connector 30b may bound a portion of the first cell 20a. The shape of the second connector 30b may comprise a rotation of the first connector 30a about the centroid 22 of the first cell 20a. In some embodiments, all of the cells 20 and connectors 30 included in the stent 10 may follow this configuration. In some embodiments, only the interior cells 20 may follow this configuration, while end cells 20 do not. An end cell may be bounded in part by a serpentine band 14 located at an end of the stent 10.

A reference circle about a circumference of the stent 10 may pass through the centroid 22 of a cell 20, and may divide the cell into two portions. The second portion of the cell 20 may be shaped according to a rotation of the first portion of the cell 20 about the centroid 22 of the cell, and vice versa. In some embodiments, all of the cells 20 and connectors 30 included in the stent 10 may follow this configuration. In some embodiments, only the interior cells 20 may follow this configuration, while end cells 20 do not.

Each connector 30 may have a first end 32 and a second end 34. The first end 32 may be longitudinally and circumferentially offset from the second end 34. Longitudinal offset means that a line between the first end 32 and the second end 34 will have a component that runs in the longitudinal direction of the stent 10. Circumferential offset means that a line between the first end 32 and the second end 34 will have a component that runs in a circumferential direction of the stent 10.

A third connector 30c and a fourth connector 30d may comprise a pair 40 of connectors and may overlap one another under compressive loading. The third connector 30c may comprise a rotation of the first connector 30a about the centroid 22 of the second cell 20b. The fourth connector 30d may comprise a rotation of the second connector 30b about the centroid 22 of the second cell 20b.

When the stent 10 is subject to certain bending or compressive strains, the first connector 30a and second connector 30b may move toward one another and may overlap. The third connector 30c and fourth connector 30d may move toward one another and overlap. The first connector 30a and the third connector 30c may move away from one another.

The cells 20 and connectors 30 between the second serpentine band 14b and a third serpentine band 14c may be shaped according to an offset mirror image of the cells 20 and connectors 30 between the first serpentine band 14a and the second serpentine band 14b. For example, a fourth cell 20d may comprise an offset mirror image of the second cell 20b. The mirror image may be taken about the longitudinal axis 15 of the second serpentine band 14b.

Cells 20 of similar shape may spiral helically about the stent 10. For example, the second cell 20b, fourth cell 20d, a fifth cell 20e and a sixth cell 20f may spiral helically about the stent 10.

In some embodiments, a stent 10 or expandable framework 12 may be used to place Guglielmi detachable coils. The stent 10 may be delivered to a deployment location, such as an aneurysm site, and expanded. A Guglielmi detachable coil may be delivered to the location and may be maneuvered through the cells 20 of the stent 10 and into the aneurysm. In some embodiments, a stent 10 may have first cells 20a and second cells 20b alternating in the stent circumferential direction. A second cell 20b may be larger than a first cell 20a. The larger second cells 20b may be desirable for placing Guglielmi detachable coils, the coils are more easily maneuvered through the larger cell openings.

Figure 7:
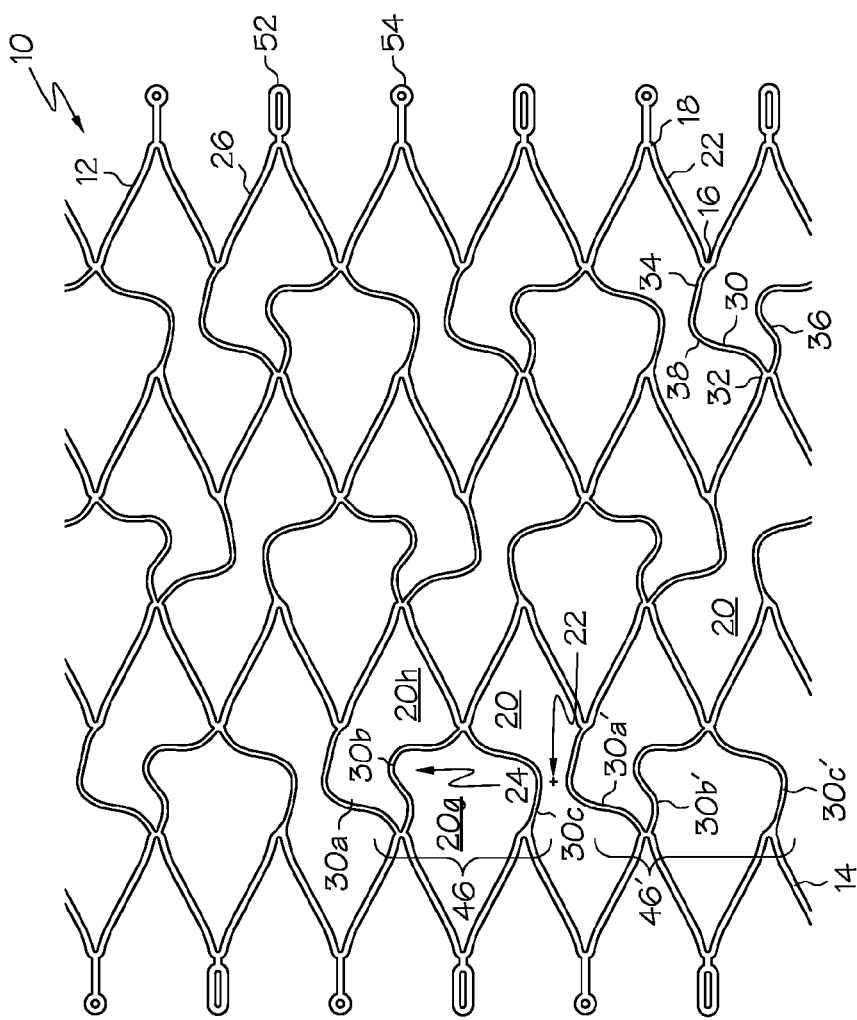
FIG. 7 is a flat pattern of another embodiment of a stent.

FIG. 7 shows another embodiment of a stent 10. The stent 10 may comprise an expandable framework 12 having a plurality of cells 20. The framework 12 may include a plurality of serpentine bands 14 and a plurality of connectors 30. Each serpentine band 14 may have alternating peaks 16 and valleys 18 connected by struts 26. Each connector 30 may connect at the first end 32 to one serpentine band 14 and may connect at the second end 34 to an adjacent serpentine band. Connectors 34 may connect to a serpentine band 14 at any portion of the band 14, and desirably at the peaks 16 and valleys 18.

The peaks 16 of adjacent serpentine bands 14 may be aligned with one another in a direction parallel to the longitudinal axis of the stent 10. The valleys 18 of adjacent serpentine bands 14 may also be aligned with one another in a direction parallel to the longitudinal axis of the stent 10.

Connectors 30 may be curved along their length and desirably include at least one peak 38. In some embodiments, connectors 30 may include at least one inflection point 36 or multiple inflection points 36. Connectors may further include any number of peaks 38 and/or valleys 39.

A first connector 30a, a second connector 30b and a third connector 30c may comprise a set 46. The first connector 30a and second connector 30b may connect to a common portion of a serpentine band 14, such as a valley 18. The second connector 30b and third connector 30c may connect to a common portion of a serpentine band 14, such as a peak 16.

The third connector 30c may be shaped according to a rotation of the first connector 30a. The center of the rotation may be a point 24 which comprises the centroid of an area including the two cells between the first connector 30a and the third connector 30c, labeled as cells 20g and 20h in FIG. 7.

The first connector 30a of a set may overlap with the third connector 30c of an adjacent set under certain conditions, such as when the stent is in an unexpanded state or when the stent is under curvature in an expanded state. For example, the first connector 30a' of connector set 46' may overlap the third connector 30c of connector set 46.

The third connector 30c of a given set 46 may be shaped according to a rotation of the first connector 30a of an adjacent set 46' about the centroid 22 of the cell separating the given set 46 from the adjacent set 46'.

The connectors 30 of a given set 46 may be similar to the connectors 30 of an adjacent set 46'. For example, connector 30a may be shaped and oriented similarly to connector 30a', connector 30b may be shaped and oriented similarly to connector 30b' and connector 30c may be shaped and oriented similarly to connector 30c'.

In some embodiments, stents 10 may include marker tabs 52 which may be used to support radiopaque markers which can be seen under fluoroscopy. Marker tabs 52 may be connected to outward peaks 16 and/or valleys 18 of serpentine bands 14 at the ends of the stent 10.

In some embodiments, stents 10 may include holding tabs 54 for holding the stent 10, for example during chemical processing. Holding tabs 54 may be removed from the stent 10 before use in a bodily lumen. In some embodiments, holding tabs 54 may comprise electropolishing tabs which may be used to conduct electrical current through the stent. Electropolishing tabs may include an aperture 56. A conductor for supplying electrical current may be looped through the aperture 56 and/or otherwise about the electropolishing tabs.

Figure 8:
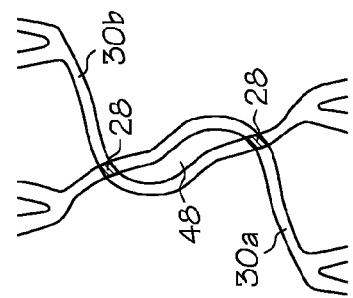
FIG. 8 shows a pair of overlapping connectors.

Referring to FIG. 8, a first connector 30a and a second connector 30b are shown in an overlapping relationship. A crossing point 28 may comprise a point where a first connector 30a and a second connector 30b overlap in a stent radial direction. Overlapping connectors may further define an area of overlap 48. The area of overlap 48 may be bounded by portions of the overlapping connectors 30a, 30b which span between crossing points 28. As the amount of overlap O (see FIG. 5) increases, the area of overlap 48 desirably increases accordingly. As the amount of curvature along the stent longitudinal increases, the area of overlap 48 may also increase.

In some embodiments, in a nominal expanded configuration of a stent without curvature, a first connector and a second connector may be non-overlapping. Upon crimping of the expanded stent to an unexpanded configuration, the first connector may overlap the second connector.

In some embodiments, in a nominal expanded configuration of a stent without curvature, a first connector and a second connector may be non-overlapping. Upon applying curvature to the stent along its length, the first connector may overlap the second connector.

Figure 9:
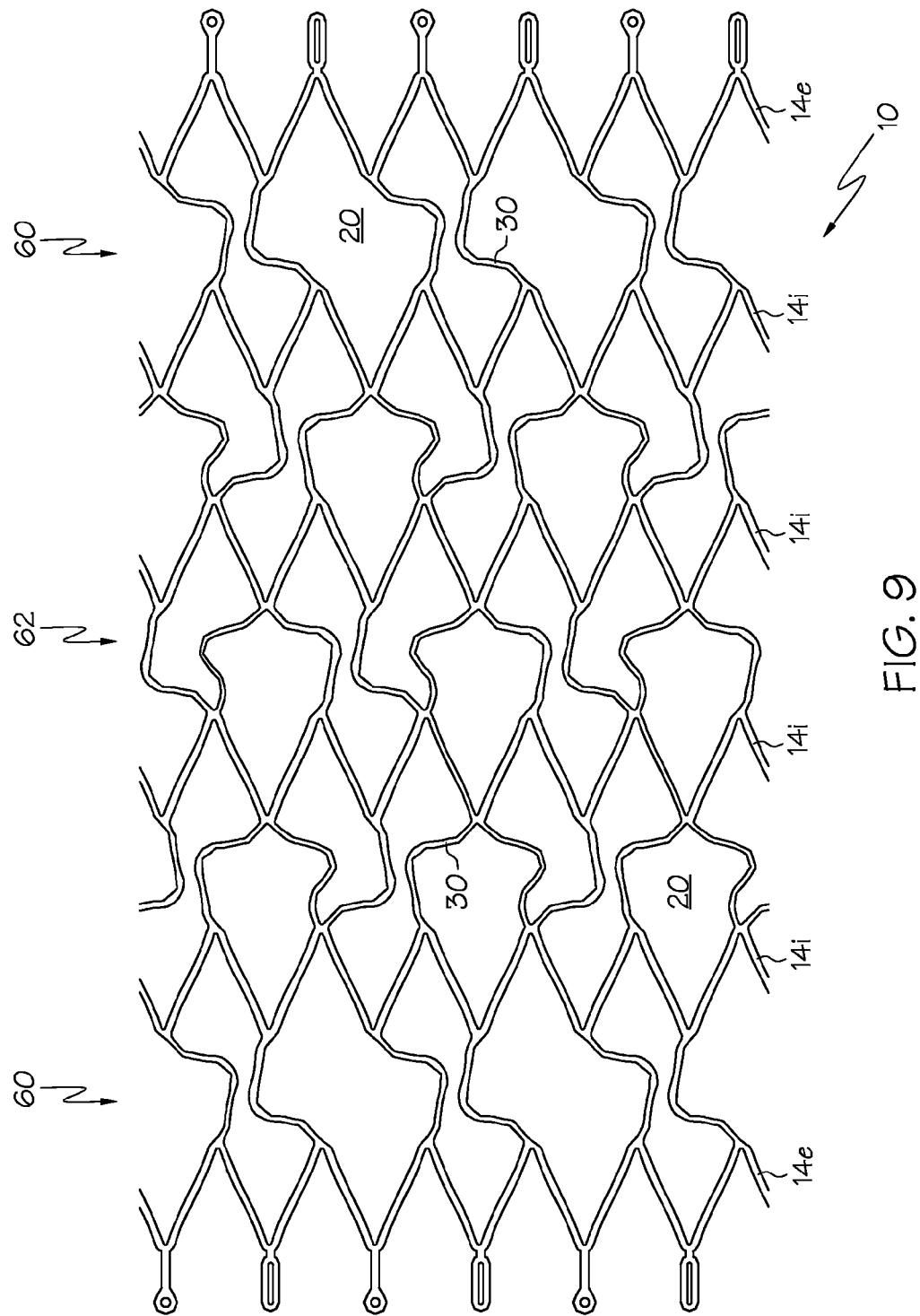
FIG. 9 is a flat pattern of another embodiment of a stent.

FIG. 9 shows another embodiment of a stent 10. Areas of the stent 10 located between two interior serpentine bands 14i may include a greater number of cells 20 than areas of the stent 10 located between an interior serpentine band 14i and an end serpentine band 14e. Areas of the stent 10 located between two interior serpentine bands 14i may include a greater number of connectors 30 than areas of the stent 10 located between an interior serpentine band 14i and an end serpentine band 14e. Areas of the stent 10 located between two interior serpentine bands 14i may include three types of connectors 30, while areas of the stent 10 located between an interior serpentine band 14i and an end serpentine band 14e may include two types of connectors.

Any of the features disclosed herein with respect to any embodiment of a stent may be combined with any other features disclosed herein to form additional embodiments. For example, the stent 10 shown in FIG. 9 includes first connector columns 60 and second connector columns 62. First connector columns 60 may be located between an interior serpentine band 14i and an end serpentine band 14e. Second connector columns 62 may be located between two interior serpentine bands 14i. The cells 20 and connectors 30 located in first connector columns 60 may be similar to the cells and connectors described with respect to FIG. 1. The cells 20 and connectors 30 located in second connector columns 62 may be similar to the cells and connectors described with respect to FIG. 7. Features of any other figures may be similarly combined.

In another embodiment, second connector columns 62 may be located between an interior serpentine band 14i and an end serpentine band 14e, and first connector columns 60 may be located between two interior serpentine bands 14i.

In some embodiments, a stent may be formed according to the following numbered paragraphs:

1. A stent comprising a plurality of serpentine bands, adjacent serpentine bands connected by connectors, wherein a first connector and a second connector overlap in a radial direction of the stent when the stent includes curvature along a longitudinal axis; wherein no connector overlaps more than one connector in a radial direction of the stent.
2. The stent of paragraph 1 above, wherein the first connector and the second connector overlap in a radial direction of the stent when the stent is unexpanded.
3. The stent of paragraph 1 above, wherein the amount of overlap increases as the degree of curvature along a longitudinal axis of the stent increases when the stent is expanded.
4. The stent of paragraph 1 above, wherein edges of the first connector and the second connector are rounded.
5. The stent of paragraph 1 above, wherein the width of a serpentine band strut is greater than the width of a connector.
6. The stent of paragraph 1 above, wherein the shape and orientation of the first connector and the second connector are related through a symmetry operation.
7. The stent of paragraph 6 above, wherein the second connector is a rotation of the first connector.
8. The stent of paragraph 7 above, wherein the rotation is a half-turn about a centroid of a cell between the first connector and the second connector.
9. The stent of paragraph 7 above, further comprising a third connector and a fourth connector, the third connector being a reflection of the first connector and the fourth connector being a reflection of the second connector.
10. The stent of paragraph 1 above, wherein the serpentine bands each comprise alternating peaks and valleys; each peak and valley located on the interior of the stent having a connector extending therefrom.
11. The stent of paragraph 10 above, wherein every other peak of a first serpentine band has two connectors extending therefrom.
12. The stent of paragraph 1 above, wherein the plurality of serpentine bands includes a first serpentine band and a second serpentine band; the first connector connects at a first end to the first serpentine band and connects at a second end to the second serpentine band; and the second connector connects at a first end to the first serpentine band and connects at a second end to the second serpentine band.
13. The stent of paragraph 1 above, wherein each pair of adjacent serpentine bands are connected by at least two connectors.
14. The stent of paragraph 1 above, wherein portions of the first connector and second connector that overlap in a stent radial direction comprise crossing points, wherein the stent further comprises an area of overlap bounded by portions of the first connector and the second connector which span between crossing points, and the area of overlap increases as the curvature of the stent increases.

Any of the inventive stents disclosed above may be provided with a uniform diameter or may taper in portions or along the entire length of the stent. Also, the width and/or thickness of the various portions of the inventive stents may increase or decrease along a given portion of the stent. For example, the width and/or thickness of the serpentine bands and/or connectors may increase or decrease along portions of the stent or along the entire length of the stent. The amplitude and wavelength of several successive first serpentine bands may remain constant while the width and/or thickness of the successive first serpentine bands decrease. Similarly, the amplitude and wavelength of several successive second serpentine bands may remain constant while the width and/or thickness of the successive second serpentine bands decrease.

The inventive stents may also be provided with end effects by modifying the stent such that that one or both ends are more rigid or more flexible than the remainder of the stent. Any of the inventive stents disclosed herein may be modified to have proximal-most and/or distal-most serpentine bands of a greater total circumferential length than the remaining serpentine bands. Any of the inventive stents disclosed herein may also be modified to have proximal-most and/or distal-most serpentine bands of a lesser total circumferential length than the remaining serpentine bands. Moreover, any of the inventive stents disclosed herein may also be modified so that one of the ends has serpentine bands of a lesser total circumferential length than the serpentine band of the other end which in turn is longer or shorter than the total length of any of the remaining serpentine bands.

Also, one or both of the end serpentine bands may be modified to be of a greater longitudinal extent than the remaining serpentine bands or to be of a lesser longitudinal extent than the remaining serpentine bands. Each of the two end serpentine bands may differ in longitudinal extent with one another and with the remaining serpentine bands.

The invention also contemplates modifying the ends of any of the inventive stents so that the two proximal-most and/or two distal-most serpentine bands have more connections therebetween than the remaining serpentine bands or fewer connections therebetween than the remaining serpentine bands.

Further, the proximal-most and/or distal-most serpentine bands may be of a greater mass than the remaining bands or a lower mass than the remaining bands. They may be thicker than the remaining bands or thinner than the remaining bands.

It is understood that the above discussed modifications resulting in end effects may be applied to multiple serpentine bands at one or both ends of the stent and are not limited to the proximal-most and distal-most serpentine bands.

The stents disclosed herein may also be modified by employing different types of connections between the serpentine bands. To that end, any of the connectors and connector configurations disclosed herein may be used in any of the disclosed embodiments. The connectors may extend from peaks to valleys, from peaks to peaks, from valleys to peaks and/or from valleys to valleys.

The stents disclosed herein may also be modified by changing the number of connections between adjacent serpentine bands. Thus, where larger cells are desired, fewer connections between serpentine bands will be provided. Where smaller cells are desired, more connections between bands will be provided. Any of the embodiments shown may also be modified in some portions of the stent but not others. Thus, some sections of the stent may have more connections and other sections may have fewer connections. More flexibility may be achieved by providing fewer connections between adjacent serpentine bands.

The connectors may range in width from being wider than the width of the widest struts in the stent, to being narrower than the narrowest struts in the stent or anywhere in between. Regions of different flexibility in the stent may also be achieved by using wider connectors in some regions, for example on one or both of the ends of the stent, and narrower connectors in the other regions of the stent (e.g. the middle) or vice versa.

In various embodiments, the struts 26 of a serpentine band 14 may be straight, curved or may have any other suitable shape. For example, struts 26 may have any number of peaks and/or valleys.

The invention also contemplates embodiments in which the spacing between adjacent serpentine bands varies in different portions of the stent. For example, the proximal-most serpentine band and/or the distal-most serpentine band may be spaced further apart from the serpentine bands adjacent thereto or may space closer thereto. This would result in using longer connectors between the end bands or shorter connectors, depending on the configuration. In one embodiment, both the proximal-most and the distal-most serpentine bands are more closely spaced to adjacent serpentine bands than the spacing between the remaining serpentine bands and further, the spacing between the proximal-most serpentine band and the serpentine band adjacent thereto differs from the spacing between the distal-most serpentine band and the serpentine band adjacent thereto.

It is also within the scope of the invention for any of the stents disclosed herein to have connectors extending from regions other than peaks and valleys or corners of peaks and valleys. For example, the connectors may extend from positions midway between adjacent peaks and valleys, from positions one quarter of the way between peaks and valleys, from positions three quarters of the way between peaks and valleys or anywhere else between peaks and valleys.

The 'phase relationship' between adjacent serpentine bands may also be modified in any of the embodiments. For example, in some embodiments of the invention, the peaks of adjacent cylindrical bands may be in longitudinal alignment with one another or may be unaligned with one another in the longitudinal direction. Similarly, peaks on one band may be longitudinally aligned with valleys on an adjacent serpentine band or may be unaligned with valleys on an adjacent serpentine band. Some of the adjacent serpentine bands may be aligned while other adjacent bands may not be aligned. Further, the phase relationship between adjacent serpentine bands may change as the stent expands. For example, adjacent serpentine bands may be aligned in an unexpanded state and unaligned in an expanded state, or vice versa.

The stent patterns disclosed herein may also be used for bifurcated stents. One or more legs and/or the trunk of a bifurcated stent may be provided with any of the stent designs disclosed herein.

The inventive stents may be manufactured using known stent manufacturing techniques. Suitable methods for manufacturing the inventive stents include laser cutting, chemical etching or stamping of a tube. The inventive stents may also be manufactured by laser cutting, chemically etching, stamping a flat sheet, rolling the sheet and, optionally, welding the sheet. Other suitable manufacturing techniques include electrode discharge machining or molding the stent with the desired design. The stent may also be manufactured by welding individual sections, for example, serpentine bands, together. Any other suitable stent manufacturing process may be performed on the stent to manufacture the stent and to achieve desirable stent characteristics. For example, a stent may be processed using sandblasting, brushing, chemical etching, electropolishing and the like.

In one embodiment, a stent may be laser cut from a tube and then chemically processed to achieve the desired shapes and dimensions of the various framework elements, such as the connector cross-section as shown in FIG. 6.

In some embodiments, the framework of a self-expanding stent may be cut from a tube of shape-memory material in a nominal expansion state. The framework may then be expanded to a full expanded size, and then may be crimped onto a catheter.

Any suitable stent material may be used in the manufacture of the inventive stents. Examples of such materials include polymeric materials, metals, ceramics and composites. Suitable polymeric materials include thermotropic liquid crystal polymers (LCP's). Where the stent is made of metal, the metal may be stainless steel, cobalt chrome alloys such as elgiloy, tantalum or other plastically deformable metals. Other suitable metals include shape-memory metals such as nickel-titanium alloys generically known as "nitinol", platinum/tungsten alloys and titanium alloys.

The invention also contemplates the use of more than one material in the inventive stents. For example, the first serpentine band and the second serpentine band may be made of different materials. Optionally, the connectors may be made of a different material than the serpentine bands.

The inventive stents may be provided in mechanically expandable form, in self-expanding form or as a hybrid of the two. Mechanically expandable stents, in accordance with the invention, may be expanded using any suitable mechanical device including a balloon.

The inventive stents may include suitable radiopaque coatings. For example, the stents may be coated with gold or other noble metals or sputtered with tantalum or other metals. The stents may also be made directly from a radiopaque material to obviate the need for a radiopaque coating or may be made of a material having a radiopaque inner core. Other radiopaque metals which may be used include platinum, platinum-tungsten, palladium, platinum-iridium, rhodium, tantalum, or alloys or composites of these metals.

In some embodiments, the stent may comprise one or more therapeutic agents. In some embodiments the agent is placed on the stent in the form of a coating. In at least one embodiment the coating includes at least one therapeutic agent and at least one polymer agent.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The inventive stents may also be used as the framework for a graft. Suitable coverings include, but are not limited to nylon, collagen, PTFE and expanded PTFE, polyethylene terephthalate and KEVLAR, Nitinol such as thin film Nitinol or any of the materials disclosed in U.S. Pat. No. 5,824,046 and U.S. Pat. No. 5,755,770. More generally, any known graft material may be used including synthetic polymers such as polyethylene, polypropylene, polyurethane, polyglycolic acid, polyesters, polyamides, their mixtures, blends and copolymers.

The inventive stents may find use in coronary arteries, renal arteries, peripheral arteries including iliac arteries, arteries of the neck and cerebral arteries. The stents of the present invention, however, are not limited to use in the vascular system and may also be advantageously employed in other body structures, including but not limited to arteries, veins, biliary ducts, urethras, fallopian tubes, bronchial tubes, the trachea, the esophagus, the prostate and the bowels.

Suitable stent delivery devices such as those disclosed in U.S. Pat. No. 6,123,712, U.S. Pat. No. 6,120,522 and U.S. Pat. No. 5,957,930 may be used to deliver the inventive stents to the desired bodily location. The choice of delivery device will depend on whether a self-expanding or balloon expandable stent is used. The inventive stents may be delivered in conjunction with one or more stent retaining sleeves. An example of stent retaining sleeves is disclosed in US provisional application 60/238,178.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of various embodiments of the invention. Those skilled in the art may recognize other equivalents to the specific embodiments described herein which equivalents are intended to be encompassed by the claims attached hereto.

The invention claimed is:

1. A stent formed from a single piece of material, the stent comprising:
   a plurality of serpentine bands, said serpentine bands located adjacent one another in a stent longitudinal direction, each serpentine band consisting of elements that do not overlap in a stent radial direction; and
   a plurality of connectors, each connector attached to and spanning between two adjacent serpentine bands;
   wherein a first connector and a second connector overlap in a stent radial direction when the stent is in an unexpanded orientation, and said first connector and said second connector do not overlap when the stent is in an expanded orientation.

2. The stent of claim 1, wherein said first connector overlaps only said second connector.

3. The stent of claim 1, wherein said first connector comprises an asymmetrical shape.

4. The stent of claim 3, wherein said first connector and said second connector comprise a similar shape and have different orientations.

5. The stent of claim 1, wherein said first connector comprises an inflection point.

6. The stent of claim 1, comprising a plurality of cells including first cells and second cells, said first cells shaped differently from said second cells.

7. The stent of claim 6, wherein said first cells and said second cells alternate in a stent circumferential direction.

8. The stent of claim 1, wherein said first connector and said second connector comprise a connector pair, said stent further comprising a plurality of connector pairs, each connector pair comprising one connector that overlaps another connector in a stent radial direction.

9. The stent of claim 1, wherein said first connector and said second connector overlap at a first location and at a second location.

10. The stent of claim 1, formed by a process comprising removing material from a tube.

11. The stent of claim 1, wherein said first connector comprises rounded edge portions.

12. The stent of claim 11, wherein said second connector comprises rounded edge portions.

13. The stent of claim 1, further comprising a holding tab located at an end of the stent.

14. A stent formed from a single piece of material, the stent comprising:
   a plurality of serpentine bands, said serpentine bands located adjacent one another in a stent longitudinal direction, each serpentine band consisting of elements that do not overlap in a stent radial direction; and
   a plurality of connectors, each connector attached to and spanning between two adjacent serpentine bands;
   wherein a first connector and a second connector overlap in a stent radial direction, said first connector and said second connector comprise a connector pair, said stent further comprising a plurality of connector pairs, each connector pair comprising one connector that overlaps another connector in a stent radial direction;
   further comprising a connector that is never overlapped by another connector.

15. A stent formed from a single piece of material, the stent comprising:
   a plurality of serpentine bands, said serpentine bands located adjacent one another in a stent longitudinal direction, each serpentine band consisting of elements that do not overlap in a stent radial direction; and
   a plurality of connectors, each connector attached to and spanning between two adjacent serpentine bands;
   wherein a first connector and a second connector overlap in a stent radial direction, said first connector and said second connector comprise a connector pair, said stent further comprising a plurality of connector pairs, each connector pair comprising one connector that overlaps another connector in a stent radial direction;
   further comprising a connector that is not overlapped by another connector.

* * * * *